(12) United States Patent (10) Patent No.: US 9,234,236 B2
Thomas et al. (45) Date of Patent: Jan. 12, 2016

(54) MICROFLUIDIC CHIP FEATURES FOR OPTICAL AND THERMAL ISOLATION

(71) Applicant: Canon U.S. Life Sciences, Inc., Rockville, MD (US)

(72) Inventors: Bradley S. Thomas, Timonium, MD (US); Johnathan S. Coursey, Rockville, MD (US); Kenton C. Hasson, Germantown, MD (US); Hongye Liang, Clarksville, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 14/508,173

(22) Filed: Oct. 7, 2014

(65) Prior Publication Data

US 2015/0118738 A1 Apr. 30, 2015

Related U.S. Application Data

(62) Division of application No. 13/674,528, filed on Nov. 12, 2012, now Pat. No. 8,852,527, which is a division of application No. 12/779,523, filed on May 13, 2010, now Pat. No. 8,329,117.

(60) Provisional application No. 61/178,233, filed on May 14, 2009.

(51) Int. Cl.
*G01N 15/06* (2006.01)
*G01N 33/00* (2006.01)
(Continued)

(52) U.S. Cl.
CPC .............. *C12Q 1/686* (2013.01); *B01L 3/5027* (2013.01); *B01L 7/52* (2013.01); *B01L 2300/0858* (2013.01); *B01L 2300/18* (2013.01); *G01N 21/0303* (2013.01); *Y10T 436/11* (2015.01)

(58) Field of Classification Search
USPC ........... 422/502, 503, 68.1; 436/43, 164, 165, 436/172
See application file for complete search history.

(56) References Cited

U.S. PATENT DOCUMENTS 5,965,410 A 10/1999 Chow et al.
6,132,580 A 10/2000 Mathies et al.
(Continued)

FOREIGN PATENT DOCUMENTS

WO 2005/075683 A1 8/2005

OTHER PUBLICATIONS

Kopp et al., "Chemical Amplification: Continuous-Flow PCR on a Chip," Science, vol. 280, (1998) pp. 1046-1048.
(Continued)

*Primary Examiner* — Brian J Sines
(74) *Attorney, Agent, or Firm* — Rothwell, Figg, Ernst & Manbeck, P.C.

(57) ABSTRACT

A microfluidic chip includes microfluidic channels, elements for thermally and optically isolating the microfluidic channels, and elements for enhancing the detection of optical signal emitted from the microfluidic channels. The thermal and optical isolation elements may comprise barrier channels interposed between adjacently-arranged pairs of microfluidic channels for preventing thermal and optical cross-talk between the adjacent microfluidic channels. The isolation element may alternatively comprise reflective film embedded in the microfluidic chip between the adjacent microfluidic channels. The signal enhancement elements comprise structures disposed adjacent to the microfluidic channels that reflect light passing through or emitted from the microfluidic channel in a direction toward a detector. The structures may comprise channels or a faceted surface that redirects the light by total internal reflection or reflective film material embedded in the microfluidic chip.

7 Claims, 8 Drawing Sheets

(51) Int. Cl.
*C12Q 1/68* (2006.01)
*B01L 3/00* (2006.01)
*B01L 7/00* (2006.01)
*G01N 21/03* (2006.01)

(56) References Cited

U.S. PATENT DOCUMENTS

| | | | |
|---|---|---|---|
| 6,174,675 | B1 | 1/2001 | Chow et al. |
| 6,875,619 | B2 | 4/2005 | Blackburn |
| 6,906,797 | B1 * | 6/2005 | Kao et al. .................. 356/317 |
| 6,960,437 | B2 | 11/2005 | Enzelberger et al. |
| 7,373,035 | B2 | 5/2008 | Sims |
| 7,939,033 | B2 | 5/2011 | Lavric et al. |
| 2003/0155344 | A1 | 8/2003 | Cobb |
| 2003/0226604 | A1 | 12/2003 | Schlautmann et al. |
| 2004/0053334 | A1 | 3/2004 | Ratner et al. |
| 2005/0042639 | A1 | 2/2005 | Knapp et al. |
| 2006/0012793 | A1 | 1/2006 | Harris |
| 2006/0083473 | A1 | 4/2006 | Ticknor et al. |
| 2006/0188979 | A1 | 8/2006 | Spaid et al. |
| 2006/0257069 | A1 | 11/2006 | Sims |
| 2008/0003588 | A1 | 1/2008 | Hasson et al. |
| 2008/0003594 | A1 | 1/2008 | Hasson et al. |

OTHER PUBLICATIONS

Lagally et al., "Single-Molecule DNA Amplification and Analysis in an Integrated Microfluidic Device," Analytical Chemistry, vol. 73, No. 3, (2001) pp. 565-570.
Park et al., "Cylindrical compact thermal-cycling device for continuous-flow polymerase chain reaction," Analytical Chemistry, vol. 75 (2003) pp. 6029-6033.
Poser et al., "Chip elements for fast thermocycling," Sensors and Actuators A, vol. 62, pp. 672-675 (1997) (abstract).
Schneegass et al., "Flow-through polymerase chain reactions in chip thermocyclers," Reviews in Molecular Biotechnology, vol. 82, pp. 101-121 (2001) (abstract).

* cited by examiner

MICROFLUIDIC CHIP FEATURES FOR OPTICAL AND THERMAL ISOLATION

RELATED APPLICATIONS

This application is a divisional of and claims priority to U.S. patent application Ser. No. 13/674,528, filed on Nov. 12, 2012, which is a divisional of and claims priority to U.S. patent application Ser. No. 12/779,523, filed on May 13, 2010, now U.S. Pat. No. 8,329,117 issued Dec. 11, 2012, which claims the benefit of provisional application Ser. No. 61/178,233, filed May 14, 2009, each of which are incorporated herein by reference in their entirety.

BACKGROUND

1. Field of the Invention

This invention relates to microfluidic devices having multiple microfluidic channels through which reaction materials flow and, more specifically, to microfluidic devices having features for effecting optical and thermal isolation of microfluidic channels in microfluidic devices.

2. Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. Polymerase Chain Reaction ("PCR") is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR, see *Real-Time PCR: An Essential Guide*, K. Edwards et al., eds., Horizon Bioscience, Norwich, U.K. (2004).

A number of commercial instruments exist that perform real-time PCR. Examples of available instruments include the Applied Biosystems PRISM 7500, the Bio-Rad iCylcer, and the Roche Diagnostics LightCycler 2.0.

More recently, a number of high throughput approaches to performing PCR and other amplification reactions have been developed, for example, involving amplification reactions in microfluidic devices, as well as methods for detecting and analyzing amplified nucleic acids in or on the devices. Thermal cycling of the sample for amplification in microfluidic devices is usually accomplished in one of two methods. In the first method, the sample solution is loaded into the device and the temperature is cycled in time, much like a conventional PCR instrument. In the second method, the sample solution is pumped continuously through spatially varying temperature zones. See, e.g., Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Microfluidic chips are being developed for "lab-on-a-chip" devices to perform in-vitro diagnostic testing. The largest growth area is in molecular biology where DNA amplification is performed in the sealed channels of the chip. Optical detection devices are commonly used to measure the increasing amplicon product over time (Real Time PCR) or to perform a thermal melt to identify the presence of a specific genotype (High Resolution Thermal Melt). Exemplary disclosures related to the imaging of a microfluidic chip to measure the fluorescent product can be found in commonly-owned U.S. application Ser. No. 11/505,358 to Hasson et al. entitled "Real-Time PCR in Micro Channels" (U.S. Pat. Pub. 2008-0003588) and U.S. application Ser. No. 11/606,204 to Hasson et al. entitled "Systems and Methods for Monitoring the Amplification and Dissociation Behavior of DNA Molecules" (U.S. Pat. Pub. 2008-0003594), the respective disclosures of which are hereby incorporated by reference.

A general trend in in-vitro diagnostic microfluidic chips is to make them smaller to conserve sample volumes, material cost, biohazard waste volume, and to reduce thermal mass of the chip for faster PCR cycling. The down side of this size reduction, however, is the increased difficulty in isolating fluidic channels—both thermally and optically—from each other.

Thermal separation of microfluidic channels is a more significant issue if the design has individual heaters for independent thermal cycling in each channel. Independent thermal cycling does not necessarily mean that each channel is driven on a different cycle, which is the extreme of control systems. Even if temperature cycling is performed in unison (i.e., simultaneously in all channels), if there is a separate, dedicated heating element for each channel, there is a potential thermal isolation issue. When one channel is higher or lower than a setpoint temperature, the control system needs to compensate locally. Deviation from setpoint temperature could be caused by varying wattages due to the heating element manufacturing tolerances or by greater heat loss which can occur at the edges of the microfluidic chip, thereby causing lower temperatures in channels adjacent to the edge of the chip. The response to changing inputs to individual heater elements must be isolated in order to create an effective closed loop control. If a significant portion of energy from surrounding heater elements conducts into or out of the area of the heating element for which control input is being adjusted, the response will be hard to predict because of the surrounding influences. The control algorithms may be able to compensate if the surrounding influences were steady state, but in this case they are also being actively controlled. This makes each channel less predictable and may make the system unstable. Improving channel-to-channel isolation by reducing or preventing thermal crosstalk between adjacent channels will improve control of the individual channel temperatures.

Optical isolation of the microfluidic channels is also a problem for some detection systems. As the size of microfluidic chips shrinks, the fluid volume within each channels is reduced, which consequently reduces emission signal levels. Also, as channels through which fluorescent indicators flow are also moved closer together this promotes emission signal crosstalk between adjacent channels. The clear glass or polymer microfluidic chip creates light pipe paths between channels which enables greater crosstalk.

When all channels are illuminated simultaneously, emitted fluorescent light intensity is the critical parameter for detection. Even though the excitation light is basically unidirectional from a single source, the emission light is omni-directional. It is possible, therefore, for one channel to have no emission and light emitted from adjacent channels crosses into the non-emitting one and through particle scattering or refraction at the walls, some light is turned toward the detector. This can elevate signal levels or give false signals.

Also, being omni-directional, most of the emission light does not propagate in the direction of the detector. Much of the light is transmitted through the surface of the micro chip opposite the detector. Accordingly, the intensity of the emission light that actually reaches the detector can be very small, making accurate measurements problematic.

This phenomenon is illustrated in FIGS. 1 and 2. FIG. 1 shows a schematic representation of a partial transverse cross-section of a microfluidic chip 10 having a number of microfluidic channels 16, 18, 20 formed therein. Incident excitation light, represented by arrows 22, is directed through the incident surface 12 at channel 18, light passing through channel 18 toward an opposite surface 14 of the chip 10 is represented by arrows 24, and light reflected or refracted toward adjacent channels 16, 20 is represented by arrows 26, 28, respectively. As shown in FIG. 2, emission light from the channel 18 at which the excitation light 22 is directed is represented by arrows 30. A portion of the emission light 30 is directed at the adjacent channels 16 and 20, as represented by arrows 32 and 34, respectively. The light 26, 32 incident on channel 16 and the light 28, 34 incident on channel 20 may cause emissions from channels 16 and 20, as represented by arrows 36 and 38, respectively. A portion of the emission light 36, 38 from the adjacent channels 16, 20, respectively, will be directed toward the incident surface 12, as represented by arrows 40 and 42, toward the detector (not shown), thereby causing an inaccurate signal strength signal from the channel 18 and/or false signals from the adjacent channels 16, 20.

Also, much of the emission light 30 from the channel 18 will be directed toward surface 14 and will not be detected by the detector that is above surface 12, thus resulting in a relatively weak emission signal from channel 18.

Accordingly, a need exists for a microfluidic chip having means for preventing thermal and optical cross-talk between adjacent microfluidic channels and further for capturing more of the omni-directional emission light from a channel.

SUMMARY

The present invention encompasses systems and methods for providing an optical and/or thermal barrier between adjacently oriented microfluidic channels to reduce or prevent optical and/or thermal cross-talk between the adjacent channels. Other aspects of the invention encompass systems and methods for providing reflective features that reflect back toward a detector at least a portion of the light passing through or emanating from a microfluidic channel.

Accordingly, aspects of the invention are embodied in a microfluidic device comprising at least first and second microfluidic channels and a barrier channel interposed between at least a portion of the first microfluidic channel and a portion of the second microfluidic channel. The barrier channel contains a material that is of lower refractive index than a material forming the microfluidic channels and is configured to reduce transfer of heat and/or light between the microfluidic channels.

According to another aspect, the microfluidic device comprises a plurality of microfluidic channels and a barrier channel interposed between at least a portion of each pair of adjacent microfluidic channels.

According to another aspect, at least one segment of the first microfluidic channel is substantially parallel to at least one segment of the second microfluidic channel. The barrier channel is interposed between the parallel segments of the first and second microfluidic channels and is substantially parallel to the microfluidic channels.

According to another aspect, the material forming the microfluidic channels comprises glass. In other embodiments, the material forming the microfluidic channels is plastic.

According to another aspect, the barrier channel is filled with a gas selected from the group consisting of air, argon, carbon dioxide, krypton, SF6, or any mixture of two or more of air, argon, carbon dioxide, krypton, or SF6.

According to another aspect, the barrier channel has one or more channel sides which form angles to adjacent microfluidic channel sides such that the barrier channel side transversely reflects light arriving at the barrier side from the adjacent microfluidic channel.

According to another aspect, the barrier channel is trapezoidal in axial cross-section and includes opposed parallel sides and opposed angled sides. The angled sides face the first and second microfluidic channels. According to another aspect, the angled sides are oriented at an angle of approximately 45 degrees to the parallel sides.

According to another aspect, at least a portion of a surface of the device comprises a reflecting surface configured to cause light passing through or emanating from the microfluidic channels toward the reflecting surface to be redirected by total internal reflection. According to another aspect, the reflecting surface comprises surface facets oriented at angles with respect to each other. According to another aspect, the facets are oriented at an angle of approximately 45 degrees to each other.

According to another aspect, the microfluidic device further comprises reflecting channels disposed adjacent to at least a portion of each of the microfluidic channels. The reflecting channels are configured to cause light passing through or emanating from the microfluidic channels toward the reflecting channels to be redirected by total internal reflection.

According to another aspect, the reflecting channels comprise two channels, each being triangular in axial cross-section, disposed adjacent to at least a portion of each of said first and second microfluidic channels. According to another aspect, the two channels are arranged side-by-side with the base sides of the triangular cross-sections co-planar with one another and an apex of each triangular cross-section contacting an apex of the adjacent triangular cross-section.

According to another aspect, the microfluidic device includes one or more functional segments of the first and second microfluidic channels, and barrier channels are omitted from between the microfluidic channels at each functional segment.

Other aspects of the invention are embodied in a microfluidic device which comprises at least first and second microfluidic channels. An optical isolation element is embedded in the microfluidic device and is interposed between at least a portion of the first microfluidic channel and a portion of the second microfluidic channel. The optical isolation element is adapted to reduce transfer of light between the microfluidic channels at the portions of the microfluidic channels between which the optical isolation element is interposed. A signal enhancement element is embedded in the microfluidic device and is disposed adjacent to at least a portion of each of the microfluidic channels. The signal enhancement element is configured to reflect light passing through or emanating from the microfluidic channels and impinging on the signal enhancement element.

According to another aspect, the microfluidic device includes a plurality of microfluidic channels, and an optical isolation element is interposed between at least a portion of each pair of adjacent microfluidic channels.

According to another aspect, the microfluidic device includes one or more functional segments of the first and second microfluidic channels, and the optical isolation element and the signal enhancement element are omitted from between the microfluidic channels at each functional segment.

According to another aspect, the optical isolation element comprises metal film, and the signal enhancement element comprises metal film. These metal films are preferably made of aluminum or silver. Other suitable metals include gold, platinum and nickel.

The above and other aspects and embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF PREFERRED EMBODIMENTS

Figure 1:
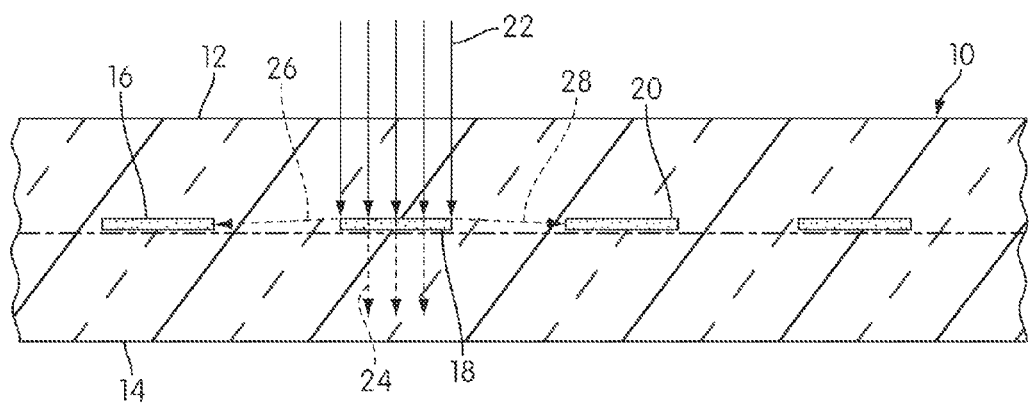
FIG. 1 is a partial, transverse cross-section of a microfluidic device in accordance with the prior art.
Figure 2:
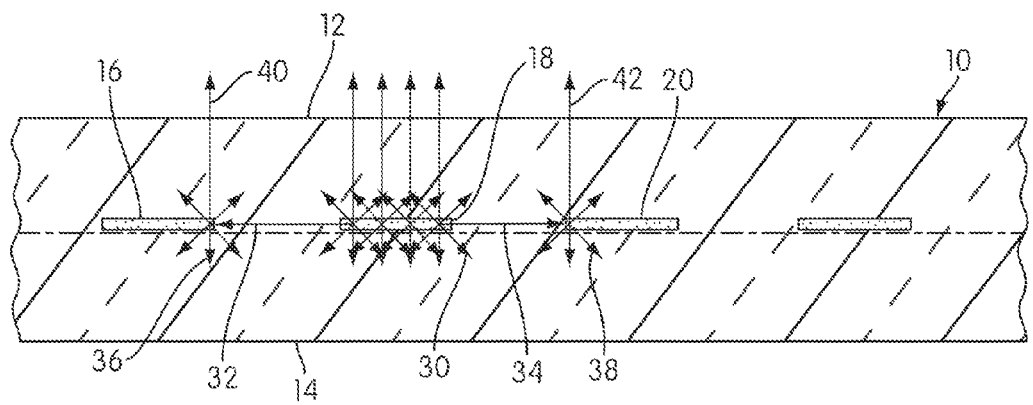
FIG. 2 is a partial, transverse cross-section of a microfluidic device in accordance with the prior art.
Figure 3:
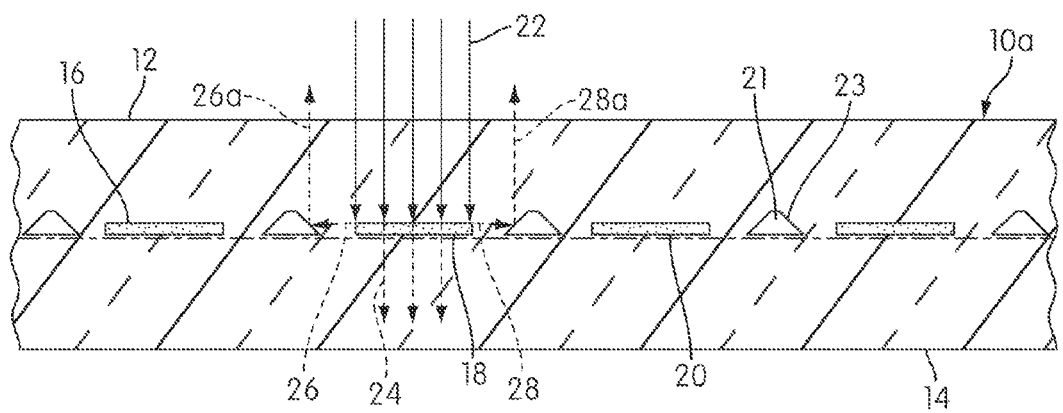
FIG. 3 is a partial, transverse cross-section of a microfluidic device in accordance with embodiments of the invention including features for limiting optical cross-talk between channels of the device and showing excitation light rays incident on a channel and redirection of light deflected from the channel toward adjacent channels.
Figure 4:
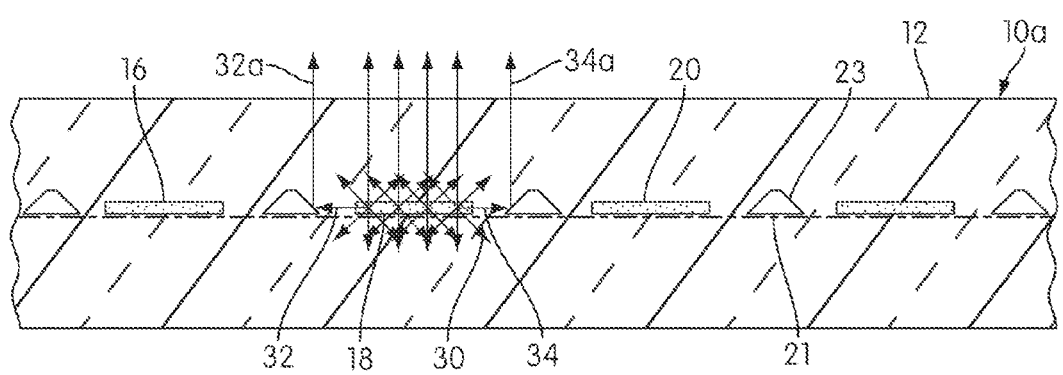
FIG. 4 is a partial, transverse cross-section of a microfluidic device in accordance with the embodiments of the invention including features for limiting optical cross-talk between channels of the device and showing emission light rays emanating from a channel and redirection of light emitted from the channel toward adjacent channels.

A microfluidic chip embodying aspects of the present invention is indicated by reference number 10a in FIGS. 3 and 4, which shows a schematic representation of a partial transverse cross-section of the microfluidic chip 10a. Microfluidic chip 10a may be made of clear glass or polymer and includes a number of microfluidic channels 16, 18, 20 formed therein and which may be parallel along portions of their lengths. The microfluidic chip 10a is illustrated in FIGS. 3 and 4 having three microfluidic channels. However, more or fewer microfluidic channels can be used. Extending between at least portions of the microfluidic channels 16, 18, 20, and oriented generally parallel thereto, are barrier channels 21. Barrier channels 21 are configured to reduce heat and/or light transfer between adjacent microfluidic channels. More specifically, to reduce heat transfer between adjacent microfluidic channels, each barrier channel 21 may be filled with a substance having relatively poor thermal conductivity. Exemplary substances exhibiting relatively poor thermal conductivity include gases, such as, air, argon, carbon dioxide, krypton, SF6, or any mixture of two or more of air, argon, carbon dioxide, krypton, or SF6. Accordingly, the barrier channel 21 so-configured effects a discontinuity in the thermal transfer path between adjacent microfluidic channels to thereby reduce thermal transfer (i.e., thermal crosstalk) between the adjacent microfluidic channels. Thus, barrier channels 21 function as thermal isolation elements which create a degree of thermal isolation of each of the microfluidic channels 16, 18, 20 by limiting the amount of thermal energy transfer between adjacent microfluidic channels.

Furthermore, to reduce light transfer between adjacent microfluidic channels, the barrier channels 21 may have angled sides 23 and may be filled with a substance having a lower index of refraction than the material of which the microfluidic chip 10a is formed. Again, suitable substances exhibiting relatively low indices of refraction include gases, such as, air, argon, carbon dioxide, krypton, SF6, or any mixture of two or more of air, argon, carbon dioxide, krypton, or SF6.

As shown in FIG. 3, incident excitation light, represented by arrows 22, is directed through the incident surface 12 of microfluidic chip 10a at channel 18, light passing through channel 18 toward an opposite surface 14 of the chip 10a is represented by arrows 24, and light reflected or refracted toward adjacent channels 16, 20 is represented by arrows 26, 28, respectively. As shown in FIG. 4, emission light from the channel 18, at which the excitation light 22 is directed, is represented by arrows 30. A portion of the emission light 30 is directed at the adjacent channels 16 and 20, as represented by arrows 32 and 34, respectively.

However, instead of impinging on channels 16 and 20, the light 26, 32 directed toward the channel 16 and the light 28, 34 directed toward the channel 20 encounter an intervening barrier channel 21. The angled sides 23 of the barrier channel 21, combined with the reduction in the index of refraction at the interface of channel 21 and the chip body, cause light impinging on the sides 23 to deflect by total internal reflection in directions away from adjacent channels 16 and 20. In one embodiment, barrier channels 21 have a trapezoidal shape with a top side and bottom side that are parallel to each other and to the incident surface 12 and opposed angled sides 23 that are oriented at 45 degrees to the top and bottom sides, as shown, to cause the light redirected by the barrier channel to be directed toward the incident surface 12, as represented by arrows 26a, 28a (FIG. 3) and 32a, 34a (FIG. 4).

Thus, barrier channels 21 also function as optical isolation elements which create a degree of optical isolation of each of the microfluidic channels 16, 18, 20 by limiting the amount of optical signal transfer (i.e., optical crosstalk) between adjacent microfluidic channels.

Figure 5:
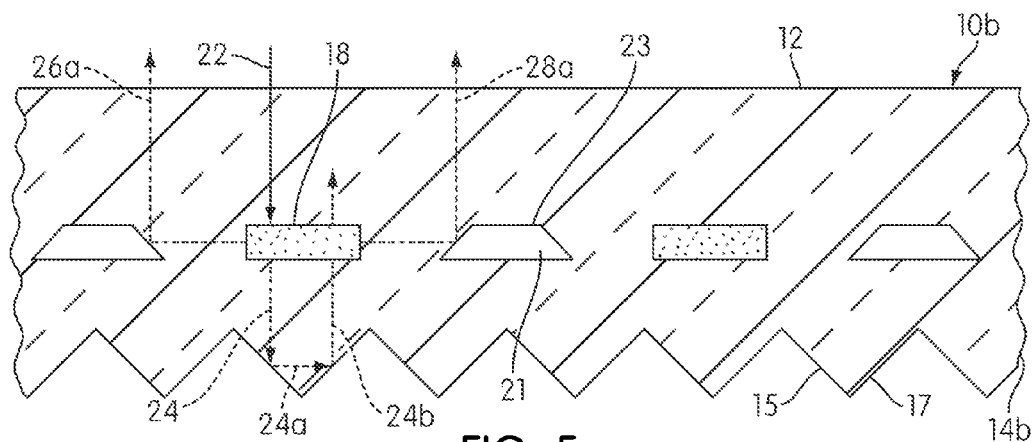
FIG. 5 is a partial, transverse cross-section of a microfluidic device in accordance with the embodiments of the invention including features for limiting optical cross-talk between channels of the device and features for reflecting light internally from a surface of the device by total internal reflection.

Another embodiment of a microfluidic chip embodying aspects of the present invention is indicated by reference number 10b in FIG. 5, which shows a schematic representation of a partial transverse cross-section of the microfluidic chip 10b. Microfluidic chip 10b is, in many respects, similar to microfluidic chip 10a shown in FIGS. 3 and 4 and includes, for example, microfluidic channel 18 and barrier channels 21 with angled sides 23. Microfluidic chip 10b differs from microfluidic chip 10a, however, in that the bottom 14b of microfluidic chip 10b is not flat as is bottom surface 14 of microfluidic chip 10a. Instead, the bottom 14b of microfluidic chip 10b is defined by a plurality of facets 15, 17 oriented at angles to each other. As shown in FIG. 5, the faceted surface of bottom 14b causes light passing through or emitted from channel 18 toward bottom 14b (as indicated by arrow 24) to be redirected at the facets 15, 17 by total internal reflection. In one embodiment, the facets 15, 17 are oriented at approximately 45 degrees relative to incident surface 12, as shown, to cause at least a portion of the light 24 redirected by the facets 15, 17 to be directed toward the incident surface 12 as represented by arrows 24a, 24b.

Thus, the facets 15, 17 of microfluidic chip 10b function as signal enhancement structures because they reflect at least a portion of the light passing through or emitted from the microfluidic channel 18 back toward the incidence surface 12 so that light can be detected, thus increasing the strength of—and thereby enhancing—the detected optical signal.

Figure 6:
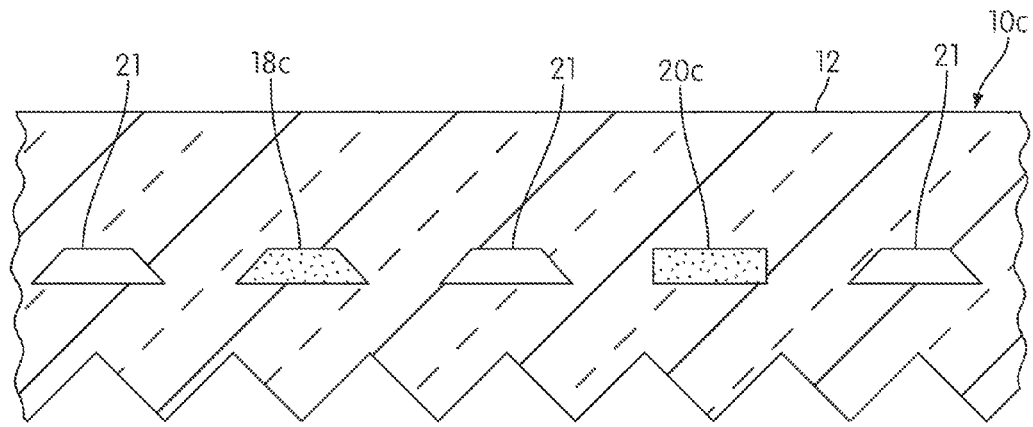
FIG. 6 is an alternative embodiment of the microfluidic device of FIG. 5.

A further embodiment of a microfluidic chip embodying aspects of the present invention is indicated by reference number 10c in FIG. 6, which shows a schematic representation of a partial transverse cross-section of the microfluidic chip 10c. Microfluidic chip 10c includes microfluidic channels 18c, 20c having the same configuration as the barrier channels 21. In the illustrated embodiment, microfluidic channels 18c, 20c, like barrier channels 21, have a trapezoidal shape with a top side and bottom side that are parallel to each other and to the incident surface 12 and opposed angled sides that are oriented at approximately 45 degrees to the top and bottom sides. Forming the microfluidic channels 18c, 20c with the same configuration as the barrier channels 21 may be desirable as it may simplify manufacture to have all channels identically configured.

Figure 7:
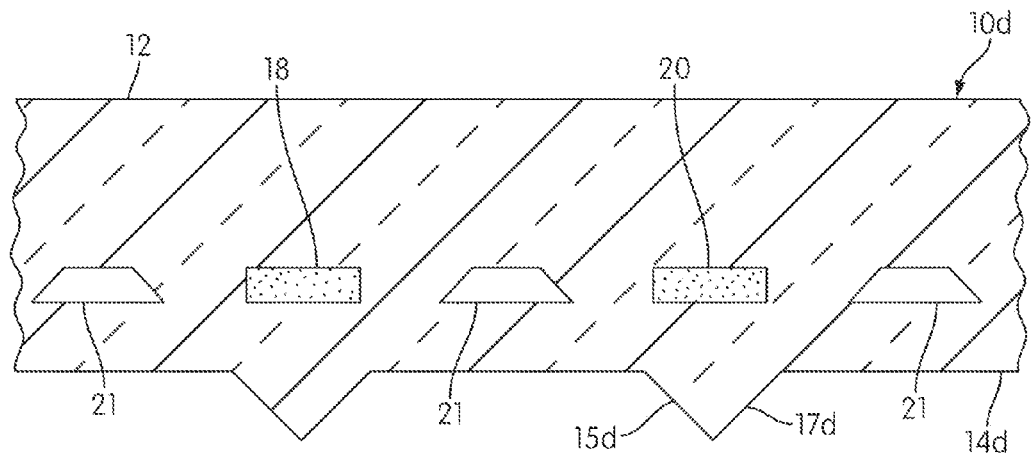
FIG. 7 is a further alternative embodiment of the microfluidic device of FIG. 5.

Another embodiment of a micro-fluidic chip embodying aspects of the present invention is indicated by reference number 10d in FIG. 7, which shows a schematic representation of a partial transverse cross-section of the microfluidic chip 10d. Microfluidic chip 10d includes a bottom portion 14d having facets 15d, 17d disposed only beneath the microfluidic channels 18, 20. In the illustrated embodiment, facets 15d, 17d are oriented at about 45 degrees to the incident surface 12. A microfluidic chip configuration such as 10d may have a reduced mass as compared to microfluidic chip configuration 10b shown in FIG. 5, yet microfluidic chip 10d would retain the ability to reflect light passing through or emitted from the microfluidic channels 18, 20 by total internal reflection.

Figure 8:
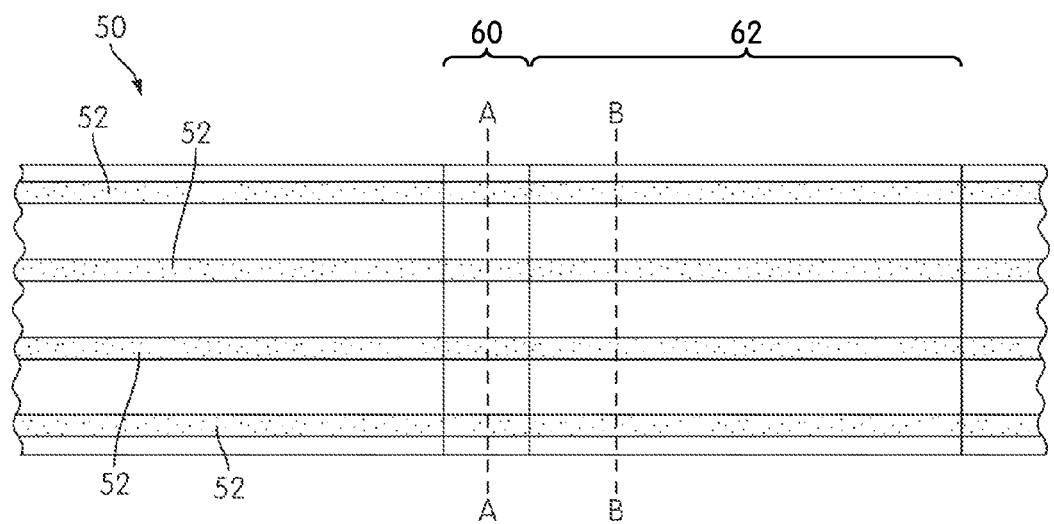
FIG. 8 is a partial plan view of a microfluidic device in accordance with embodiments of the invention including functional regions and detecting regions with optical isolation elements and signal enhancement elements.
Figure 8A:
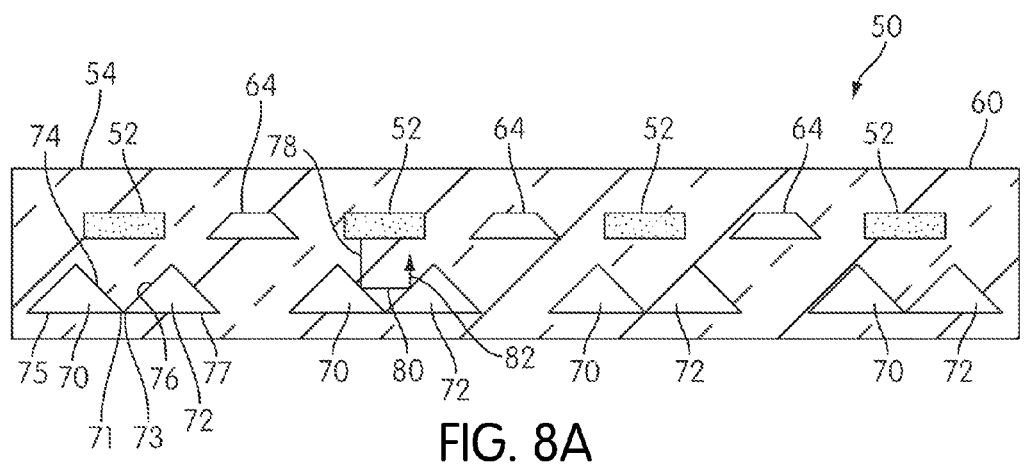
FIG. 8A is a transverse cross-section along the line A-A of FIG. 8.
Figure 8B:
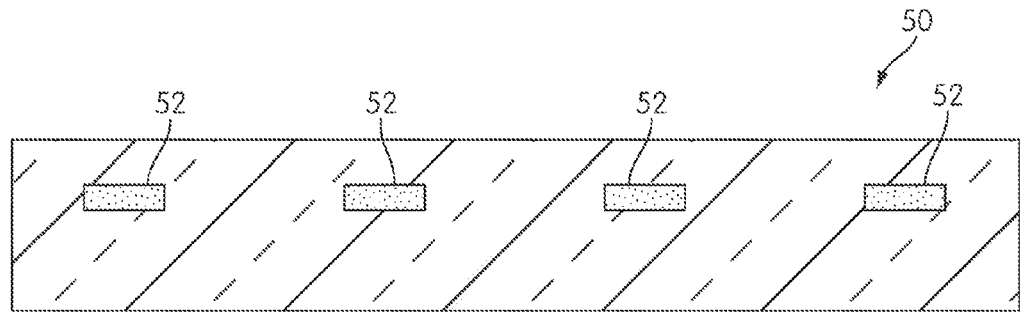
FIG. 8B is a transverse cross-section along the line B-B of FIG. 8.

A further embodiment of a microfluidic chip embodying aspects of the present invention is indicated by reference number 50 in FIGS. 8, 8A, and 8B. Microfluidic chip 50 includes a number of microfluidic channels 52 (four channels in the illustrated non-limiting embodiment), and the microfluidic chip 50 is divided into optical interrogation regions 60 and functional regions 62. As implied by the name, the optical interrogation regions 60 are sections of the lengths of the microfluidic channels 52 at which the channels are optically interrogated, such as by an optical detector adapted to detect chemiluminescence or to generate an optical excitation signal and detect emitted fluorescence. As shown in FIG. 8A, which shows the optical interrogation region 60 in cross-section, the optical interrogation regions 60 are characterized by barrier channels (i.e., optical isolation channels) 64 interposed between adjacent microfluidic channels 52 for preventing optical cross-talk between the adjacent channels. In one embodiment, barrier channels 64 have a trapezoidal shape with a top side and bottom side that are parallel to each other and to the top (incident) surface 54 and opposed angled sides that are oriented at approximately 45 degrees to the top and bottom sides, as shown, to cause the light redirected by the barrier channel 64 to be directed toward the top surface 54. In other embodiments, the barrier channel 64 could be triangular in axial cross-section. In other embodiments, the barrier channel 64 is angled sufficiently such that the impinging light 26, 32 and 28, 34 strikes the barrier channel 64 at an angle (with respect to the normal of the barrier channel surface) that is greater than the critical angle. The critical angle is equal to the arcsine of the ratio of the indices of refraction, where the ratio is the index of refraction of the material within the barrier channel divided by the index of refraction of the substrate material.

The optical interrogation region 60 further includes signal enhancement elements in the form of channels 70, 72 arranged in a side-by side configuration below each of the microfluidic channels 52. In preferred embodiments, channels 70, 72 have opposed sides 74, 76 arranged at angles to each other and are filled with a substance having a lower index of refraction than the material of which the microfluidic chip 50 is formed, such as, air, argon, carbon dioxide, krypton, SF6, or any mixture of two or more of air, argon, carbon dioxide, krypton, or SF6.

Accordingly, sides 74, 76 will reflect light passing through or emitted from channels 52 by total internal reflection, and will redirect the light upwardly toward top surface 54, as indicated by arrows 78, 80, 82.

In the illustrated embodiment, channels 70, 72 are triangular in axial cross-section with sides 74, 76 oriented at approximately 45 degrees relative to base sides 75, 77 which are substantially co-planar and parallel to top surface 54. In a preferred embodiment, channels 70, 72 contact each other at apexes 71, 73. In other embodiments, the channels 70, 72 could also be trapezoidal in axial cross-section provided the 45 degree surfaces 74, 76 remain beneath the microfluidic channel 52.

As an alternative to channels 70, 72, microfluidic chip 50 may include signal enhancement features comprising a faceted bottom surface as shown in FIGS. 5 and 7. Similarly, facets 15, 17 of microfluidic chip 10b of FIG. 5 and facets 15d and 17d of microfluidic chip 10d of FIG. 7 may be replaced by internal optically-deflecting channels, such as channels 70, 72, of microfluidic chip 50 of FIG. 8A.

Functional regions 62 are sections of the lengths of microfluidic channels 52 at which the channels 52 are not optically interrogated. Functional regions 62 may simply be extents of the channels at which material is conveyed from one portion of the microfluidic chip to another, or they may comprise extents of the channels at which other processing steps, e.g., heating, mixing, or some combination of these and/or other steps, are performed. As shown in FIG. 8B, which shows the functional region 62 in cross section, because there is no optical interrogation in the functional regions 62, there is no need for optical isolation elements (e.g., barrier channels 64) or signal enhancement elements (e.g., channels 70, 72). If heating is performed in a functional region 62, it may be desirable to provide thermal isolation barrier channels between adjacent microfluidic channels 52 to prevent, or at least limit, thermal cross-talk between adjacent microfluidic channels. Under such circumstances in which the barrier channels are provided to perform a thermal isolation function, but not an optical isolation function, such channels need not have angled sides so as to effect total internal reflection, but need only have a suitable size and shape (e.g., rectangular or circular), and be filled with a material having relatively low thermal conductivity, to provide an effective thermal barrier between adjacent microfluidic channels.

Figure 9:
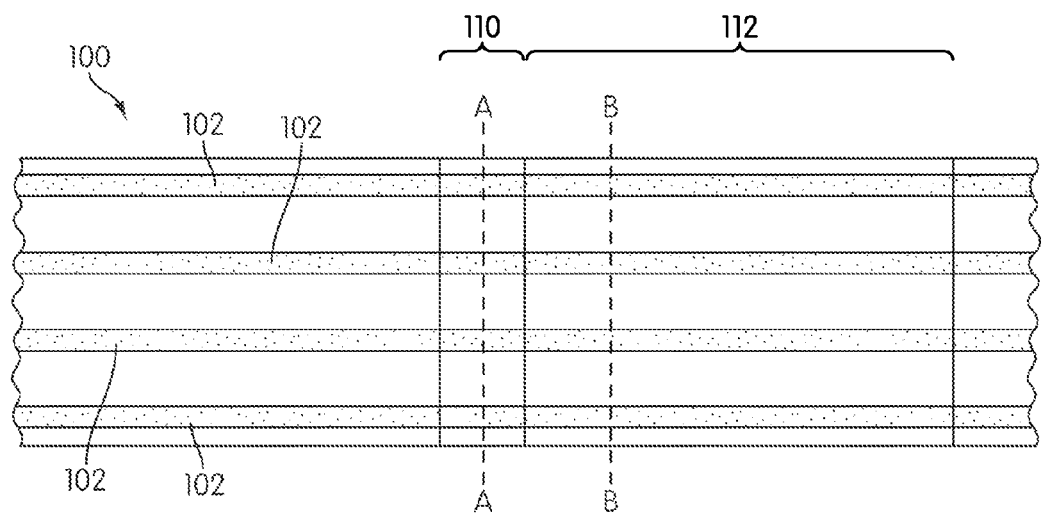
FIG. 9 is a partial plan view of an alternative embodiment of a microfluidic device including functional regions and detecting regions with optical isolation elements and signal enhancement elements.
Figure 9A:
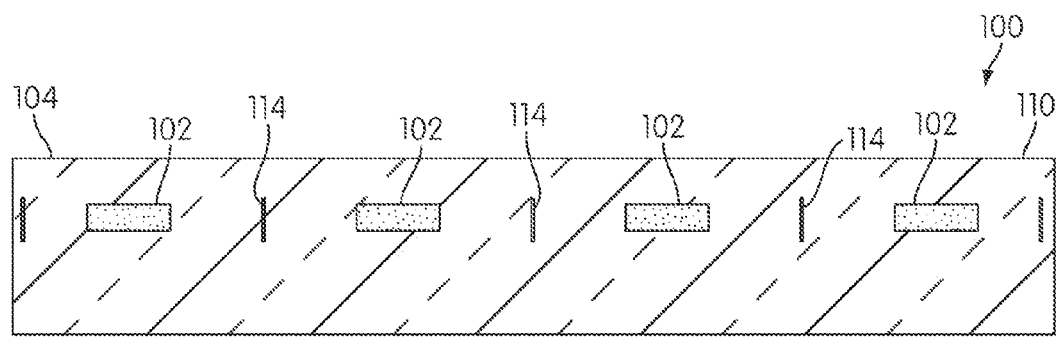
FIG. 9A is a transverse cross-section along the line A-A of FIG. 9.
Figure 9B:
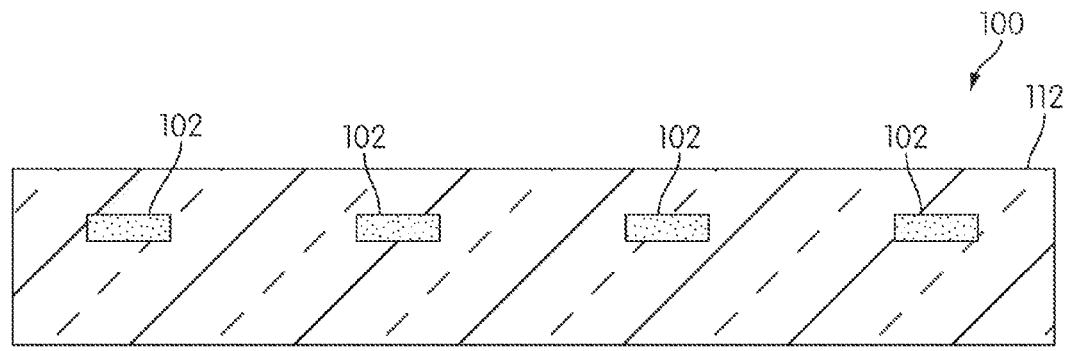
FIG. 9B is a transverse cross-section along the line B-B of FIG. 9.

A further embodiment of a microfluidic chip embodying aspects of the present invention is indicated by reference number 100 in FIGS. 9, 9A, and 9B. Microfluidic chip 100 includes a number of microfluidic channels 102 (four channels in the illustrated non-limiting embodiment), and the chip 100 is divided into sequential optical interrogation regions 110 and functional regions 112. As shown in FIG. 9A, which shows the optical interrogation region 110 in cross-section, the optical interrogation regions 110 are characterized by optical isolation elements 114 interposed between adjacent microfluidic channels 102 for preventing optical cross-talk between the adjacent channels. In one embodiment, optical isolation elements 114 comprise metal film segments (e.g., aluminum or silver) embedded into the chip 100 between pairs of adjacent microfluidic channels 102 and oriented so as to be transverse (e.g., substantially perpendicular) to a would-be straight-line optical path extending from one channel 102 to the adjacent channel 102. Other metals suitable for these metal films include gold, platinum and nickel.

The optical interrogation region 110 further includes signal enhancement elements 116 disposed below each of the microfluidic channels 102, opposite a top surface 104 at which optical detection occurs. In one embodiment, signal enhancement elements 116 comprise metal film segments (e.g., aluminum or silver) embedded into the chip 100 below microfluidic channels 102 and oriented so as to be parallel to top surface 104. Other metals suitable for these metal films include gold, platinum and nickel.

As shown in FIG. 9B, which shows functional regions 112 in cross-section, optical isolation elements (e.g., metal film segments 114) and signal enhancement elements (e.g., metal film segments 116) are omitted from functional region 112.

Figure 10:
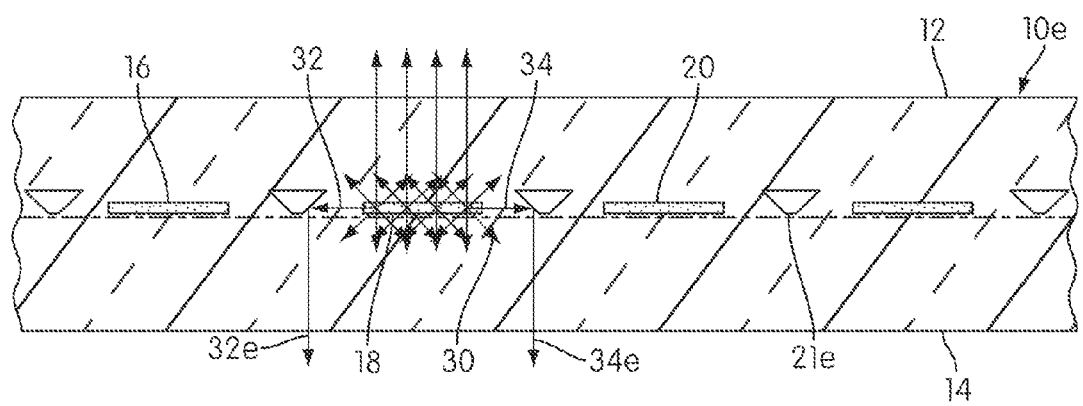
FIG. 10 is a partial, transverse cross-section of a microfluidic device in accordance with other embodiments of the invention including features for limiting optical cross-talk between channels of the device and showing emission light rays emanating from a channel and redirection of light away from the detector.

Another embodiment of a microfluidic chip embodying aspects of the present invention is indicated by reference number 10e in FIG. 10, which shows a schematic representation of a partial transverse cross-section of the microfluidic chip 10e. Microfluidic chip 10e is, in many respects, similar to microfluidic chip 10a shown in FIGS. 3 and 4 and includes, for example, microfluidic channels 16, 18, 20, incident surface 12, and bottom surface 14. Microfluidic chip 10e differs from microfluidic chip 10a, however, in that the barrier channels 21e of chip 10e are inverted, or rotated by approximately 180 degrees about their longitudinal axes, as compared to barrier channels 21 of microfluidic chip 10a. Accordingly, refracted or emitted light from channel 18, such as emitted light represented by arrows 30, that is directed at the adjacent channels 16 and 20, as represented by arrows 32 and 34, respectively, is redirected by the barrier channel 21e toward the bottom surface 14, as represented by arrows 32e, 34e, and away from a detector.

While the present invention has been described and shown in considerable detail with disclosure to certain preferred embodiments, those skilled in the art will readily appreciate other embodiments of the present invention. Accordingly, the present invention is deemed to include all modifications and variations encompassed within the spirit and scope of the following appended claims.

The invention claimed is:

1. A microfluidic device comprising:
   at least one microfluidic channel having fluorescent indicators;
   wherein the micro fluidic device comprises a reflecting surface, separate from the at least one microfluidic channel, configured to cause light passing through or emanating from the at least one microfluidic channel having fluorescent indicators toward said reflecting surface to be redirected by total internal reflection.

2. The microfluidic device of claim 1, wherein said reflecting surface comprises surface facets oriented at angles with respect to each other.

3. The microfluidic device of claim 2, wherein the facets are oriented at an angle of approximately 45 degrees with respect to each other.

4. The microfluidic device of claim 1, wherein at least a portion of the micro fluidic device comprising a reflecting surface is located only beneath the at least one microfluidic channel.

5. The microfluidic device of claim 1, wherein the material forming said microfluidic device comprises glass.

6. The microfluidic device of claim 2, wherein the surface facets function as signal enhancement structures.

7. The microfluidic device of claim 1, wherein the reflecting surface is opposite a flat surface of the microfluidic chip.

* * * * *